(12) United States Patent
Hafey et al.

(10) Patent No.: US 9,037,988 B2
(45) Date of Patent: May 19, 2015

(54) USER INTERFACE FOR PROVIDING CLINICAL APPLICATIONS AND ASSOCIATED DATA SETS BASED ON IMAGE DATA

(75) Inventors: Christopher E. Hafey, Edina, MN (US); Todd B. Johnson, Apple Valley, MN (US); Brian Diaz, Chanhassen, MN (US); Kelly Dupasquier, Eden Prairie, MN (US)

(73) Assignee: Vital Images, Inc., Minnetonka, MN (US)

( * ) Notice: Subject to any disclaimer, the term of this patent is extended or adjusted under 35 U.S.C. 154(b) by 124 days.

(21) Appl. No.: 13/513,987

(22) PCT Filed: Nov. 22, 2010

(86) PCT No.: PCT/US2010/057625
§ 371 (c)(1),
(2), (4) Date: Jul. 26, 2012

(87) PCT Pub. No.: WO2011/066222
PCT Pub. Date: Jun. 3, 2011

(65) Prior Publication Data
US 2012/0284657 A1  Nov. 8, 2012

Related U.S. Application Data

(60) Provisional application No. 61/264,580, filed on Nov. 25, 2009.

(51) Int. Cl.
G06F 17/30 (2006.01)
G06F 19/24 (2011.01)
G06Q 50/22 (2012.01)
G06F 19/00 (2011.01)

(52) U.S. Cl.
CPC .............. G06Q 50/22 (2013.01); G06F 19/321 (2013.01); *G06F 19/3487* (2013.01)

(58) Field of Classification Search
None
See application file for complete search history.

(56) References Cited

U.S. PATENT DOCUMENTS

| | | | | |
|---|---|---|---|---|
| 5,986,662 A | * | 11/1999 | Argiro et al. | 345/424 |
| 6,603,494 B1 | * | 8/2003 | Banks et al. | 715/807 |
| 6,734,880 B2 | * | 5/2004 | Chang et al. | 715/738 |
| 7,020,844 B2 | * | 3/2006 | Trevino et al. | 715/772 |
| 7,047,235 B2 | | 5/2006 | Yang et al. | |

(Continued)

OTHER PUBLICATIONS

International Search Report and Written Opinion issued in PCT/US2010/057825, mailed Jan. 18, 2011, 10 pgs.

*Primary Examiner* — Matt Kim
*Assistant Examiner* — Daniel Samwel
(74) *Attorney, Agent, or Firm* — Faegre Baker Daniels

(57) ABSTRACT

A user interface for selecting clinical applications in a medical imaging system is provided on a display and is responsive to user inputs in the medical imaging system. A request to view a study that includes a plurality of images is received. The study to be viewed is then acquired from a medical imaging system database. The acquired study is analyzed with a rule engine that executes rules on image data from the acquired study. The rule engine identifies one or more clinical applications that are appropriate for the study and identifies at least one data set from the plurality of images suited for each of the identified one or more clinical applications. One or more icons each associated with one of the identified one or more clinical applications are displayed. The one or more icons are each selectable on the user interface to initialize the associated clinical application.

20 Claims, 13 Drawing Sheets

(56) References Cited

U.S. PATENT DOCUMENTS

| | | |
|---|---|---|
| 8,031,920 B2 * | 10/2011 | Brackett .................... 382/128 |
| 2002/0143923 A1 * | 10/2002 | Alexander ................... 709/223 |
| 2003/0164860 A1 * | 9/2003 | Shen et al. .................. 345/804 |
| 2004/0009459 A1 | 1/2004 | Anderson et al. |
| 2004/0267122 A1 | 12/2004 | Nadadur et al. |
| 2006/0101053 A1 * | 5/2006 | Proctor ....................... 707/102 |
| 2006/0155579 A1 * | 7/2006 | Reid ............................... 705/2 |
| 2006/0242143 A1 * | 10/2006 | Esham et al. .................. 707/6 |
| 2008/0212861 A1 * | 9/2008 | Durgan et al. ............... 382/131 |
| 2009/0297013 A1 * | 12/2009 | Chaudhuri .................... 382/132 |
| 2010/0010827 A1 * | 1/2010 | Fueyo et al. ..................... 705/2 |
| 2010/0080427 A1 * | 4/2010 | Yeluri et al. ................. 382/128 |

\* cited by examiner

USER INTERFACE FOR PROVIDING CLINICAL APPLICATIONS AND ASSOCIATED DATA SETS BASED ON IMAGE DATA

TECHNICAL FIELD

The present invention relates to graphical user interfaces for imaging applications. More particularly, the present invention relates to a graphical user interface for providing image analysis clinical applications and the associated data sets based on stored image data.

BACKGROUND

Due to the increasingly fast processing power of modern-day computers, users have turned to computers to assist them in the examination and analysis of images of real-world data. For example, within the medical community, medical professionals who once examined x-rays hung on a light screen now use computers to examine images obtained via ultrasound, computed tomography (CT), magnetic resonance (MR), ultrasonography, positron emission tomography (PET), single photon emission computed tomography (SPECT), magnetic source imaging, and other imaging techniques.

Each of the above-identified imaging procedures generates volume images, although each relies on a different technology to do so. For example, CT uses an x-ray source to rapidly rotate around a patient to obtain up to hundreds of electronically stored pictures of the patient. On the other hand, MR uses radio-frequency waves that are emitted to cause hydrogen atoms in the body's water to move and release energy, which is then detected and translated into an image. Because each of these techniques penetrates the body of a patient to obtain data, and because the body is three-dimensional, this data represents a three-dimensional image, or volume. In particular, CT and MR both provide three-dimensional (3D) "slices" of the body, which can later be electronically reassembled.

In a radiology network may contain image information and other data about a number of different patients. The information associated with each patient may include one or more scans by one or more imaging devices. After a scan is completed, imaging software is employed to create a set of images from the raw data, called a study. A study may consist of several different views or acquisitions, such as pre- and post-contrast CT scans, or T1- and T2-weighted MR views. Each view or acquisition is generally called a series, and each series includes a number of images or slices. This hierarchy of medical image data storage is pursuant to the Digital Imaging and Communications in Medicine (DICOM) standard.

Clinical applications or protocols built into some medical imaging software systems allow a clinician to analyze images and volumes within a study using a software application built into the medical imaging software. For example, the clinician may evaluate calcium scoring or cardiac function based on one or more CT scans of the heart. In some medical imaging systems, the clinician reviews all series within a study to determine the series that is best suited for the particular application or protocol to be performed. After finding an appropriate series, the clinician then runs the desired application. This can be a cumbersome process, especially if a study includes a substantial number of series. In addition, the clinician may select a series that is less than optimal for a particular application, or the optimal volume may span across multiple different series.

SUMMARY

Disclosed is a method for generating a user interface for selecting clinical applications in a medical imaging system. The user interface is provided on a display and is responsive to user inputs in the medical imaging system. A request to view a study that includes a plurality of images is received. The study to be viewed is then acquired from a medical imaging system database. The acquired study is analyzed with a rule engine that executes a plurality of applications rules on image data from the acquired study. The rule engine identifies one or more clinical applications that are appropriate for the study and identifies at least one data set from the plurality of images suited for each of the identified one or more clinical applications. One or more icons each associated with one of the identified one or more clinical applications are displayed. The one or more icons are each selectable on the user interface to initialize the associated clinical application with the corresponding data sets.

Also disclosed is a user interface in a medical imaging system that is provided on a display and is responsive to user inputs in the medical imaging system. The user interface includes a study worklist including a selectable list of one or more studies each including a plurality of images. Selection of a study in the study worklist causes the medical imaging system to acquire the study from a medical imaging system database. The user interface also includes a data manager including one or more icons each associated with a clinical application identified by the medical imaging system as being appropriate for the selected study. Each clinical application is associated with at least one data set in the study generated from the plurality of images and identified by the medical imaging system as being suitable for the identified clinical applications.

Further disclosed is a medical imaging system including a medical imaging system database, a processor, and a display. The medical imaging system database stores one or more studies each including a plurality of images. The processor receives a request to view a study from an associated input device and accesses the medical imaging system database to acquire the requested study. The processor includes a rule engine that executes a plurality of applications rules on image data from the acquired study. The rule engine identifies one or more clinical applications that are appropriate for the study and at least one data set generated from the plurality of images that is suited for each of the identified one or more clinical applications. The display is connected to the processor and displays one or more icons each associated with one of the identified one or more clinical applications. Each of the one or more icons is selectable on the user interface with the input device to initialize the associated clinical application.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 6 is a screen shot of an example user interface including a colon study worklist having a colon study selected and a data manager including applications associated with the selected colon study.

FIG. 10 is a screen shot of an example user interface including a PET/CT study worklist having a PET/CT study selected and a data manager including applications associated with the selected PET/CT study.

Figure 1:
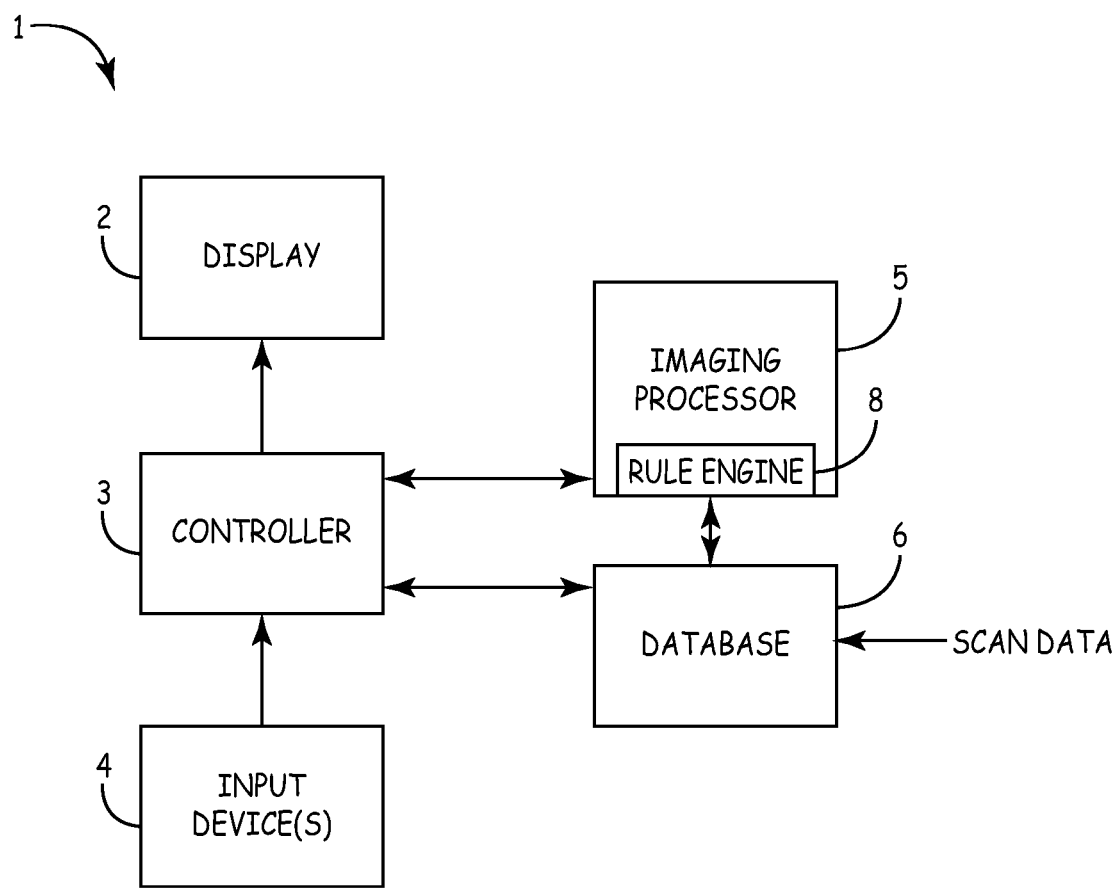
FIG. 1 is a block diagram of an embodiment of a medical imaging system that employs the user interface according to the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a block diagram of a medical imaging system 1 including a display 2, a controller 3, one or more input devices 4, an imaging processor 5, and an image database 6. The controller 3 receives inputs from the one or more input devices 4 and provides an output to the display 2. The display 2, the controller 3, and the one or more input devices 4 may be configured as a computer workstation, and the one or more input devices 4 may include, for example, a mouse, keyboard, or digital interactive pen. The controller 3 communicates with and controls both the imaging processor 5 and the image database 6. In some embodiments, the imaging processor 5 and the image database 6 are located locally with the controller 3. In other embodiments, the controller 3 communicates with and controls the imaging processor 5 and the image database 6 through the internet, such as via a web-based application run on the controller 3.

The image database 6 receives and stores data from one or more scans (e.g., CT or MR scan) of a patient, called a study. In some embodiments, the image data is sent by a Digital Imaging and Communications in Medicine (DICOM) service class user (SCU) to a DICOM service class provider (SCP). The image data may be processed prior to storing the image data in the image database 6. For example, the data from the one or more scans may be used by the imaging processor 5 to assemble the scans into a three dimensional (3D) image of the anatomical feature being analyzed. In some embodiments, the imaging processor 5 identifies data sets (e.g., volumes) from the study image data that may be used by applications run by the medical imaging system 1 to analyze anatomical features. The identified data sets may by associated with a single series of images, or may span across multiple series of images.

The imaging processor 5 may also isolate an anatomical feature of interest from the surrounding anatomy based on the response of each portion of the anatomy to the scan. For example, the anatomical feature of interest may have a different density (i.e., a different level of transparency to the scan signal) than the surrounding anatomy, and the different portions of the anatomy can thus be separated by the imaging processor 5 from each other based on this varying level of density. The imaging processor 5 may then store data related to the assembled 3D medical image in the imaging database 6.

When a user of the medical imaging system 1 wishes to analyze a study, the user may select the study via a user interface on the display 2. The studies available for analysis may be presented as a list on the display 2, and the user may use one or more of the input device(s) 4 to scroll through the study list and select the desired study for analysis. The studies shown in the study list can be filtered by keyword searching, such as words that describe the type of study (e.g., cardiac, colon, PET/CT, etc.) or names associated with the study (e.g., patient name, doctor name, etc.). The studies shown in the study list may be retrieved from the imaging database 6 or from an external medical system associated with the medical imaging system 1. Example external medical systems that may be associated with the medical imaging system 1 include, but are not limited to, a picture archiving and communication system (PACS) and/or an electronic medical record (EMR) database.

When the user selects a study on the user interface, the controller 3 queries a rule engine 8 to provide clinical applications and corresponding data sets for the selected study. The rule engine 8 retrieves the study image data from the database 6 or external medical system, which is provided to the imaging processor 5. The database 6 may also provide any preprocessed results (e.g., data sets identified from the study image data prior to storage in the database 6) that are associated with the study image data. The rule engine 8 then executes a set of rules on the study image data and any preprocessed results to identify one or more clinical applications that may be run to analyze the data. The rules executed by the rule engine 8 may be customized for a particular medical imaging site. The rule engine 8 also identifies one or more data sets from the image data that are best suited for analysis by each of the identified clinical applications. That is, the rule engine 8 associates one or more applications to the study, and associates one or more data sets to each of the applications. In some embodiments, the rule engine 8 receives other inputs to analyze the study data including, but not limited to, HL7 data with medical history, previously captured data for a patient, and user preferences.

Clinical applications (or protocols) are software applications that automate performance of specific analyses on imaging data to help assess characteristics or anomalies of an anatomical feature. Example categories of clinical applications include cardiac, vascular, neuro, oncology, CT virtual colonoscopy, and orthopedic visualization. The types of clinical applications available for use in a study is dependent on the modality used to acquire the images. For example, the following are example clinical protocols that may be applied to images acquired using a CT modality: abdominal, brain perfusion, brain analysis, cardiac: calcium scoring, cardiac: arteries, cardiac: functional, cardiac: EP planning, cardiac: myocardial, colon, generic, larynx/airway, lung, musculoskeletal, PET/CT, vascular: aorta, vascular: aorta stent, vascular: carotid, vascular: COW, vascular: renal, and vascular: runoff. As another example, the following are example clinical protocols that may be applied to images acquired using an MR modality: abdominal, brain, breast, generic, musculoskeletal, and vascular. The differences in available clinical applications for each modality are a function, at least in part, of the level of image detail produced by different image modalities.

The rule engine 8 provides a prioritized set of clinical applications and associated data sets for the selected study to the controller 3, which displays icons associated with each of the clinical applications on a data manager on the display 2. The clinical applications available in the medical imaging system 1 may be native to the system or may be third party applications integrated into the medical imaging system 1. Each icon includes an image that is related to the type of analysis performed by the associated clinical application. The icons are each selectable by the user to execute the clinical application associated with the icon. In addition, the user may view the data sets associated with each clinical application, and may view other data sets in the study that were not selected by the rule engine 8 for association with the identified clinical application. These other data sets may be selectable to override the data set or data sets identified as being suitable for the clinical application by the rule engine 8.

To illustrate the generation and use of the user interface as described, the following discussion provides examples of the process and rules considerations for three different types of studies. In particular, the first example is directed to the selection and user interface generation of a cardiac study, the second is related to a colon study, and the third is related to a PET/CT study. While each of the example studies below are associated with a single rules structure and a single category of clinical applications, it will be appreciated that studies may actually span across multiple rules structures, and may be associated with multiple categories of clinical applications.

Cardiac Study Example

Figure 2:
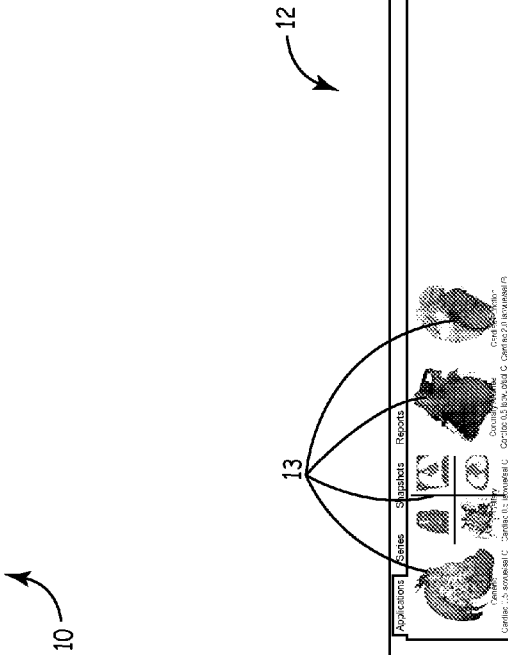
FIG. 2 is a screen shot of an example user interface including a cardiac study worklist having a cardiac study selected and a data manager including applications associated with the selected cardiac study.

FIG. 2 is a screen shot of an example user interface including a cardiac study worklist 10 having a cardiac study selected and a data manager 12 including icons 13 for clinical applications associated with the selected cardiac study. When the user initially launches the user interface shown in FIG. 2, the study worklist 10 is presented. The user may simplify the review of the studies in the worklist 10 by sorting any of the columns of information in the study worklist 10. For example, the user may select the "Patient Name" column on the study worklist 10 to sort the names of the studies in alphabetical order. As another example, the user interface may include a filter menu 14 that allows the user to filter the studies that are presented in the worklist 10 using selectable criteria (e.g., keywords, study type, study description, modality, patient gender, patient age, patient ID, physician, etc.). The user interface may also include a box to enter search text or keywords to filter the studies in the worklist 10, as is shown at the top of each column on the worklist 10.

When a user selects a study from the worklist 10, the controller 3 sends a signal to the imaging processor 5 to provide clinical applications and corresponding data sets for the selected study. The rule engine 8 retrieves the study image data from the database 6, which is provided to the imaging processor 5. The database 6 may also provide any preprocessed results (e.g., data sets identified from the study image data prior to storage in the database 6) that are associated with the study image data. The rule engine 8 then executes a set of rules that are programmed in the imaging processor 5 to the study image data and any preprocessed results to identify one or more clinical applications that may be run to analyze the data. The rule set that is retrieved and executed by the rule engine 8 may be selected based on the type of study selected by the user. Alternatively, the rule engine 8 may analyze the data retrieved from the image database 6 to identify the proper rule set.

Figure 3:
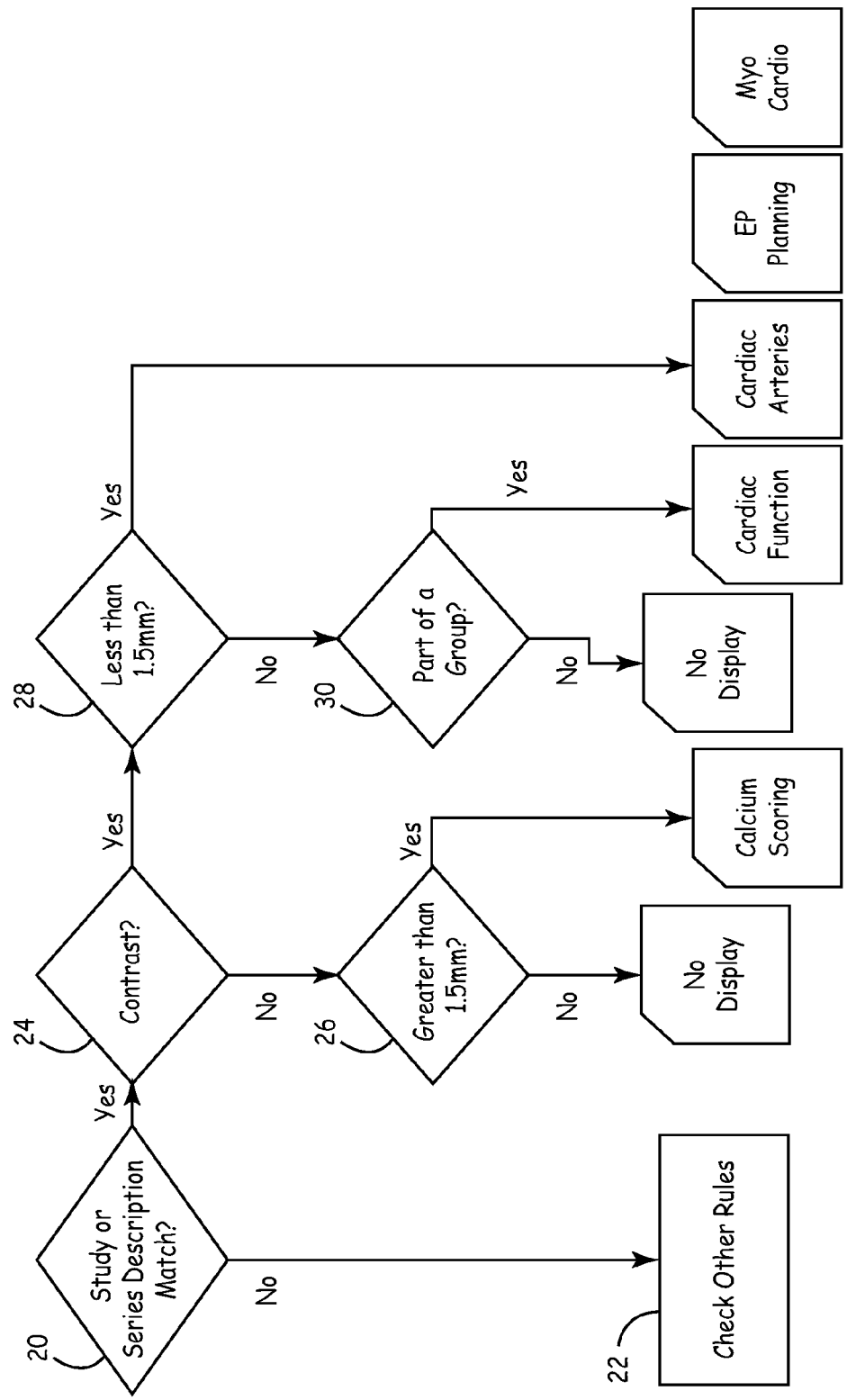
FIG. 3 is a flow diagram of a rules structure for selecting clinical applications and data sets from images associated with a selected cardiac study.

FIG. 3 is a flow diagram of an exemplary rules structure for selecting clinical applications and data sets from images associated with the selected cardiac study. In step 20, the rule engine 8 determines whether the description of the study or series matches the rules description. For example, in this embodiment, the rule engine 8 may search the "Study Description" field or other fields related to series associated with the selected study for words related to a cardiac study (e.g., cardiac, coronary, heart, calcium, score, smartscore, CACS, etc.) to determine whether the rule set based on the rules structure shown in FIG. 3 is appropriate. If words related to a cardiac study are not found in the searched field(s), then, in step 22, the rule engine 8 checks other rule sets for a keyword match with the selected study.

If a cardiac study word is found in the searched field(s) of the selected study, then the rule engine 8 begins the process of identifying suitable clinical applications and associated data sets for the selected study. In step 24, the rule engine 8 determines whether contrast agents were used during the scan to produce the images in the selected study. This information may be provided as part of the information stored with the study, or may be determined based on the scanning modality employed during the study.

If a contrast agent was not used in the selected study, in step 26 the rule engine 8 analyzes the data to determine whether features (e.g., vessels, etc.) of the data sets identified during preprocessing have a width greater than a threshold width. For example, in the embodiment shown in FIG. 3, the rule engine 8 determines whether the data set features are greater than 1.5 mm. If the data set features are greater than the threshold width, the rule engine 8 identifies the calcium scoring clinical application as suitable for analyzing the study image data. In this case, the rule engine 8 sends a signal to the controller 3 to display an icon for the calcium scoring clinical application on the data manager 12 and provides the data sets that meet the requirements for the calcium scoring clinical application to the controller 3. On the other hand, if the rule engine 8 determines that the data set features are less than or equal to the threshold width, the rule engine 8 determines that no clinical applications are suitable for the analyzing the data sets in the selected study.

If, in step 24, a contrast agent was used, then, in step 28, the rule engine 8 analyzes the data to determine whether features of the data sets identified during preprocessing have a width less than a threshold width. For example, in the embodiment shown in FIG. 3, the rule engine 8 determines whether the data set features are less than 1.5 mm. If the data set features are less than the threshold width, then the rule engine 8 identifies the cardiac arteries, electrophysiology procedure (EP) planning, and myocardial clinical applications as suitable for analyzing the study image data. In this case, the rule engine 8 sends a signal to the controller 3 to display icon for each of these clinical applications on the data manager 12 and provides the data sets that meet the requirements for each of these clinical applications to the controller 3.

If, in step 28, the rule engine 8 determines that the data set features are greater than the threshold width, then, in step 30, the rule engine 8 determines whether the data sets are part of a group of data sets that is assembled from image data produced from scans taken over a period of time. If so, the rule engine 8 identifies the cardiac function clinical application as suitable for analyzing the study image data. In this case, the rule engine 8 sends a signal to the controller 3 to display an icon for the cardiac function clinical application on the data manager 12 and provides the data sets that meet the requirements for the cardiac function clinical application to the controller 3. On the other hand, if the rule engine 8 determines in step 30 that the data sets are not a part of a group, the rule engine 8 determines that no clinical applications are suitable for analyzing the data sets in the selected study.

The rule structure for selecting applications and image data for three types of cardiac-related studies, calcium scoring, cardiac arteries, and cardiac function are expressed below in pseudocode. The pseudocode presented is not intended to be limiting, and rather is intended to illustrate one example approach to implementing the rules in the rule engine 8 described above.

Calcium Scoring Pseudocode

```
RuleDef[ ] Study_CACS = new RuleDef[3];
Study_CACS[0] = new
RuleDef(SearchColumns.STUDY_DESCRIPTION,
    "Card|Coro|Heart|Calcium|Score|CACS", MatchType.kContainsOR);
Study_CACS[1]= isNotContrast ( );
Study_CACS[2] = isThickSlice(2.5);
Study_CACS[3] = new
RuleDef(SearchColumns.NUMBER_OF_IMAGES, "5",
    MatchType.kGreaterThan);
addRule(ruleList, Study_CACS, "CARDIAC_SCORE_CT", "CT");
RuleDef[ ] Series_CACS = new RuleDef[4];
Series_CACS[0] = new
RuleDef(SearchColumns.SERIES_DESCRIPTION,
    "Card|Coro|Heart|Calcium|Score|CACS", MatchType.kContainsOR);
Series_CACS[1] = isNotContrast ( );
Series_CACS[2] = isThickSlice(2.5);
Series_CACS[3] = new
RuleDef(SearchColumns.NUMBER_OF_IMAGES, "5",
    MatchType.kGreaterThan);
addRule(ruleList, Series_CACS, "CARDIAC_SCORE_CT", "CT");
RuleDef[ ] ACQ_CACS = new RuleDef[4];
ACQ_CACS[0] = new RuleDef(SearchColumns.PROTOCOL_NAME,
"CACS|Score",
    MatchType.kContainsOR);
ACQ_CACS[1] = isNotContrast( );
ACQ_CACS[2] = isThickSlice(2.5);
ACQ_CACS[3] = new
RuleDef(SearchColumns.NUMBER_OF_IMAGES, "5",
    MatchType.kGreaterThan);
addRule(ruleList, ACQ_CACS, "CARDIAC_SCORE_CT", "CT");
```

Cardiac Arteries Pseudocode

```
RuleDef[ ] Study_CardArt= new RuleDef[4];
Study_CardArt[0] = new
RuleDef(SearchColumns.STUDY_DESCRIPTION,
    "Card|Coro|Heart|Sure", MatchType.kContainsOR);
Study_CardArt[1] = isContrast( );
Study_CardArt[2] = isThinSlice(1.5);
Study_CardArt[3] = new
RuleDef(SearchColumns.NUMBER_OF_IMAGES, "5",
    MatchType.kGreaterThan);
addRule(ruleList, Study_CardArt, "CARDIAC_ART_CT", "CT");
RuleDef[ ] Series_CardArt= new RuleDef[4];
Series_CardArt[0] = new
RuleDef(SearchColumns.SERIES_DESCRIPTION,
    "Card|Coro|Heart|Sure|%", MatchType.kContainsOR);
Series_CardArt[1] = isContrast( );
Series_CardArt[2] = isThinSlice(1.5);
Series_CardArt[3] = new
RuleDef(SearchColumns.NUMBER_OF_IMAGES, "5",
    MatchType.kGreaterThan);
addRule(ruleList, Series_CardArt, "CARDIAC_ART_CT", "CT");
RuleDef[ ] ACQ_CardArt= new RuleDef[4];
ACQ_CardArt[0] = new RuleDef(SearchColumns.PROTOCOL_NAME,
"Cardiac",
    MatchType.kContains);
ACQ_CardArt[1] = isContrast( );
ACQ_CardArt[2] = isThinSlice(1.5);
ACQ_CardArt[3] = new
RuleDef(SearchColumns.NUMBER_OF_IMAGES, "5",
    MatchType.kGreaterThan);
addRule(ruleList, ACQ_CardArt,"CARDIAC_ART_CT", "CT");
```

Cardiac Function Pseudocode

```
RuleDef[ ] Study_CardFunc= new RuleDef[2];
Study_CardFunc[0] = new
RuleDef(SearchColumns.STUDY_DESCRIPTION,
    "Card|Coro|Heart|Sure|Func", MatchType.kContainsOR);
Study_CardFunc[1] = isContrast( );
addRule(ruleList, Study_CardFunc, "CARDIAC_FUNCT_CT", "CT");
RuleDef[ ] Series_CardFunc = new RuleDef[2];
Series_CardFunc[0] = new
RuleDef(SearchColumns.SERIES_DESCRIPTION,
    "Card|Coro|Heart|Sure|Func", MatchType.kContainsOR);
Series_CardFunc[1] = isContrast( );
addRule(ruleList, Series_CardFunc, "CARDIAC_FUNCT_CT", "CT");
RuleDef[ ] ACQ_CardFunc= new RuleDef[2];
ACQ_CardFunc[0] = new
RuleDef(SearchColumns.PROTOCOL_NAME, "Cardiac",
    MatchType.kContains);
ACQ_CardFunc(1) = isContrast( );
addRule(ruleList, ACQ_Cardiac, "CARDIAC_FUNCT_CT", "CT");
```

When the clinical applications best suited for the study image data have been identified, icons representing the identified clinical applications are displayed in the data manager 12. In the embodiment shown in FIG. 2, the rule engine 8 identified the generic, coronary arteries, and cardiac function applications as being suitable for the selected study. Icons representing each of these clinical applications are displayed in the data manager 12. Also provided with the icons 13 is an icon called "Gallery" that allows the user to review all data sets associated with the study, as generated by the imaging processor 5 during preprocessing of the image data.

The icons 13 are provided on a tab on the data manager 12 entitled "Applications." The data manager 12 may also include other tabs to provide access to the data associated with the selected study in other formats. For example, if the image data is stored in the image database 6 pursuant to the DICOM standard hierarchy, the data manager 12 may include a "Series" tab that allows the user to review the all series associated with the selected study. As discussed above, the data sets that are generated for use with the clinical applications may be generated from a single series of images, or may span across multiple series of images.

Figure 4:
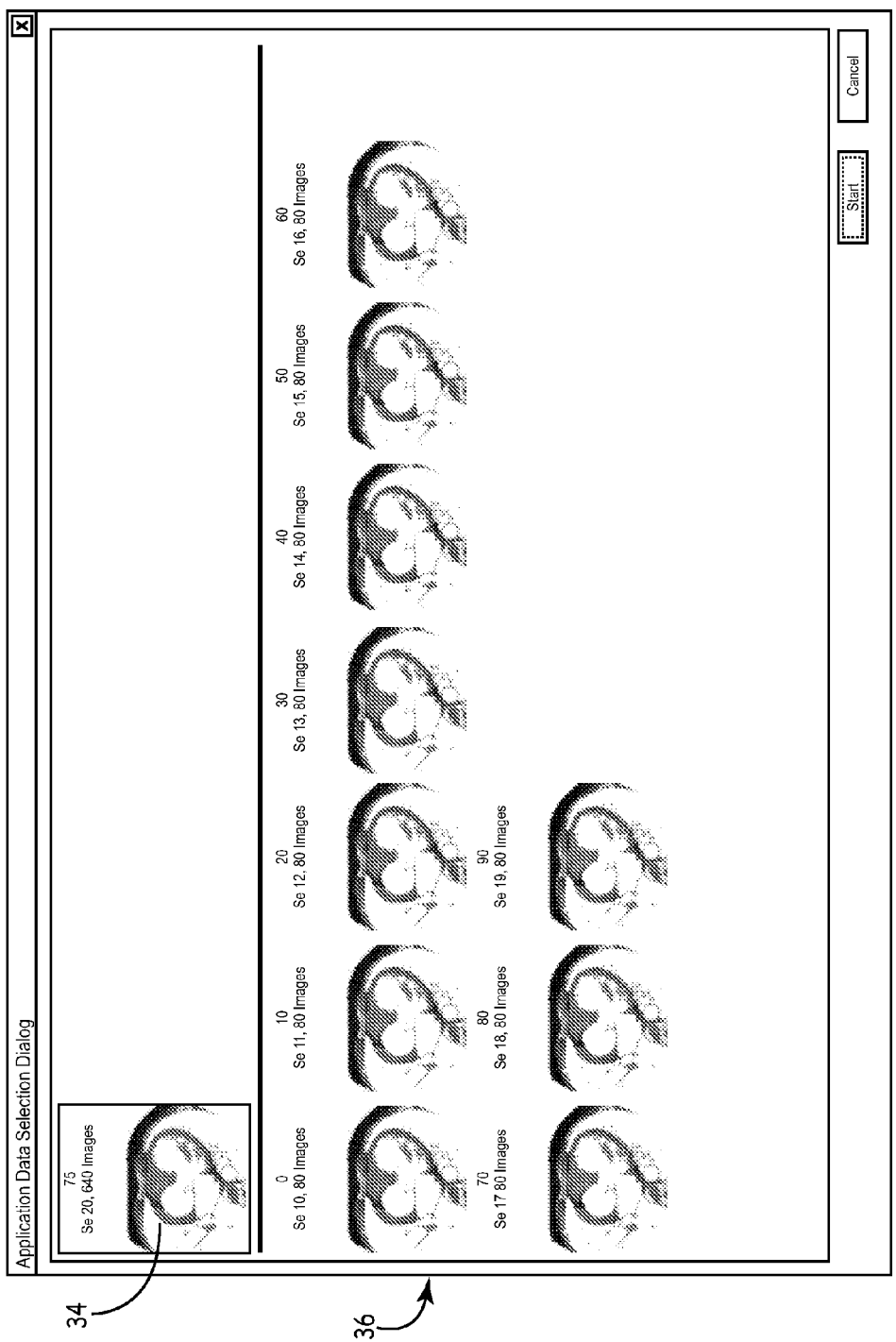
FIG. 4 is a screen shot of data sets related to a selected application in the data manager shown in FIG. 2.

The user may wish to review the data sets associated with each clinical application to make an independent assessment of the data set selection performed by the rule engine 8. FIG. 4 is a screen shot of a data selection dialog including data sets related to a selected clinical application in the data manager 12 shown in FIG. 2. The screen shot shown in FIG. 4 may accessed, for example, by right-clicking one of the clinical applications to bring up a menu and selecting an option on the menu to review the data sets associated with the application. This allows the user to see the data set(s) that were identified as being the best match for the selected clinical application. In FIG. 4, the data set that was identified by the rule engine 8 as being most suited for the selected clinical application is shown as icon 34, while other data sets that were not identified by the rule engine 8 as being suitable for the selected clinical application are shown on the bottom of the screen as icons 36. In some embodiments, a box surrounds the icon 34 to illustrate that the data set associated with icon 34 is currently associated with the selected clinical application. The user may select each of the different icons 34, 36 to view the images associated with each of the data sets. If the user thinks that one of the data sets among the icons 36 is better suited for the selected clinical application, the user can override the rule engine 8 and identify a different data set to be displayed on the upper portion of the screen. The user may replace the data set represented by icon 34 with one or more data sets represented by icons 36, or the user may add data sets represented by icons 36 to the data sets to be analyzed by the selected clinical application.

Figure 5:
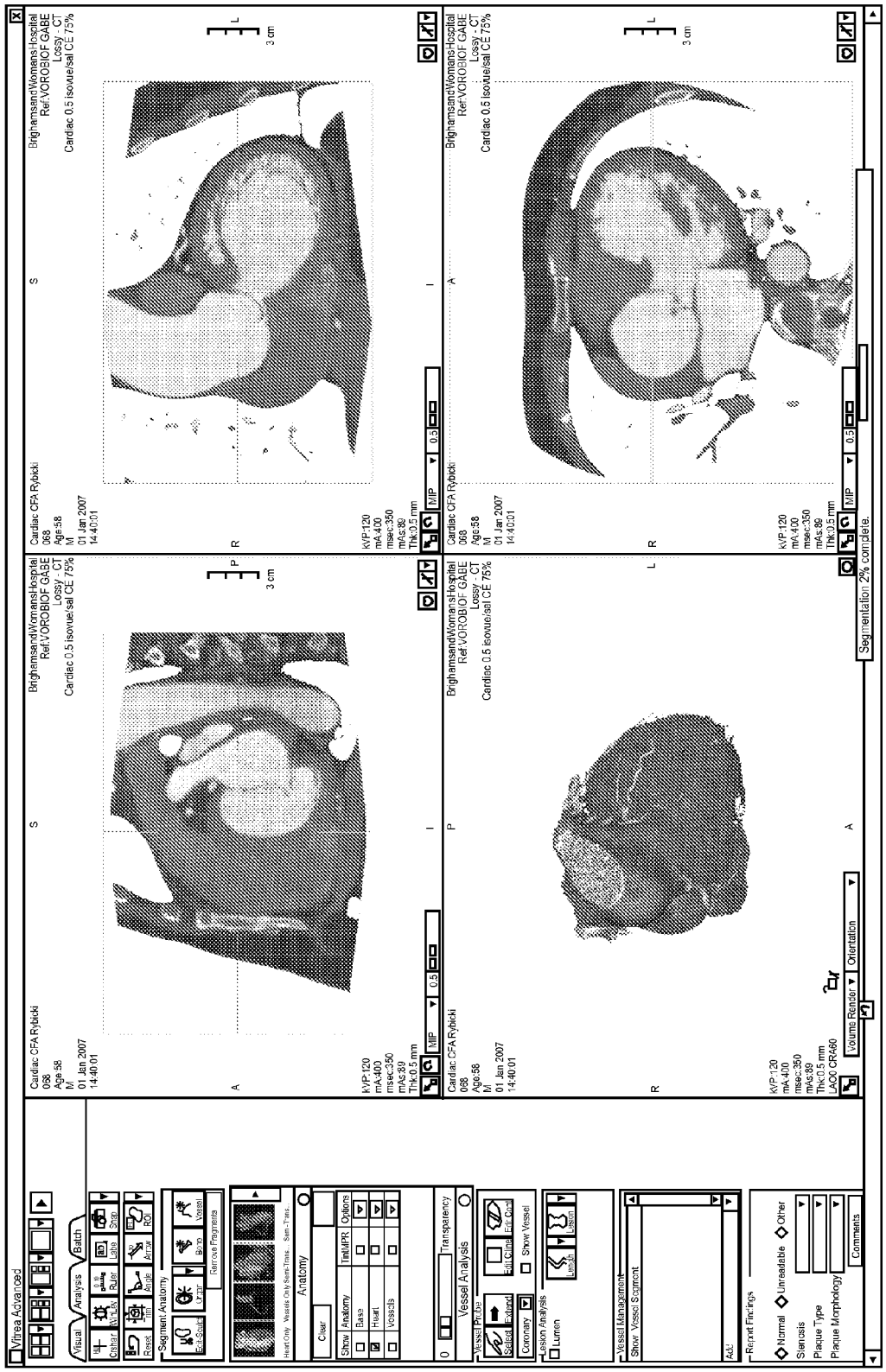
FIG. 5 is a screen shot of an application selected from the data manager in FIG. 2 loaded with a data set identified as suitable for the selected application.

When the user is satisfied with the data set(s) associated with a clinical application, the user may execute the clinical application with the selected data sets. The user may select the icon, which causes the controller 3 to begin analysis of the associated data set(s) of the clinical application. For example, FIG. 5 is a screen shot after the cardiac function clinical application is selected from the data manager 12 in FIG. 2. In this case, the initiation of the cardiac function clinical application brings up a set of tools that allows the clinician manipulate the identified data sets on the screen shown in FIG. 5 to analyze and assess various aspects cardiac function. For example, the clinician may use the application perform a visual assessment of wall motion in short and long axis orientations. The tools for the cardiac function application also allow the clinician to generate data for various cardiac parameters, such as ejection fraction, myocardial mass, and myocardial data set. The tools that are launched for each of the different types of clinical applications are specific to the particular clinical application.

Colon Study Example

Figure 6:
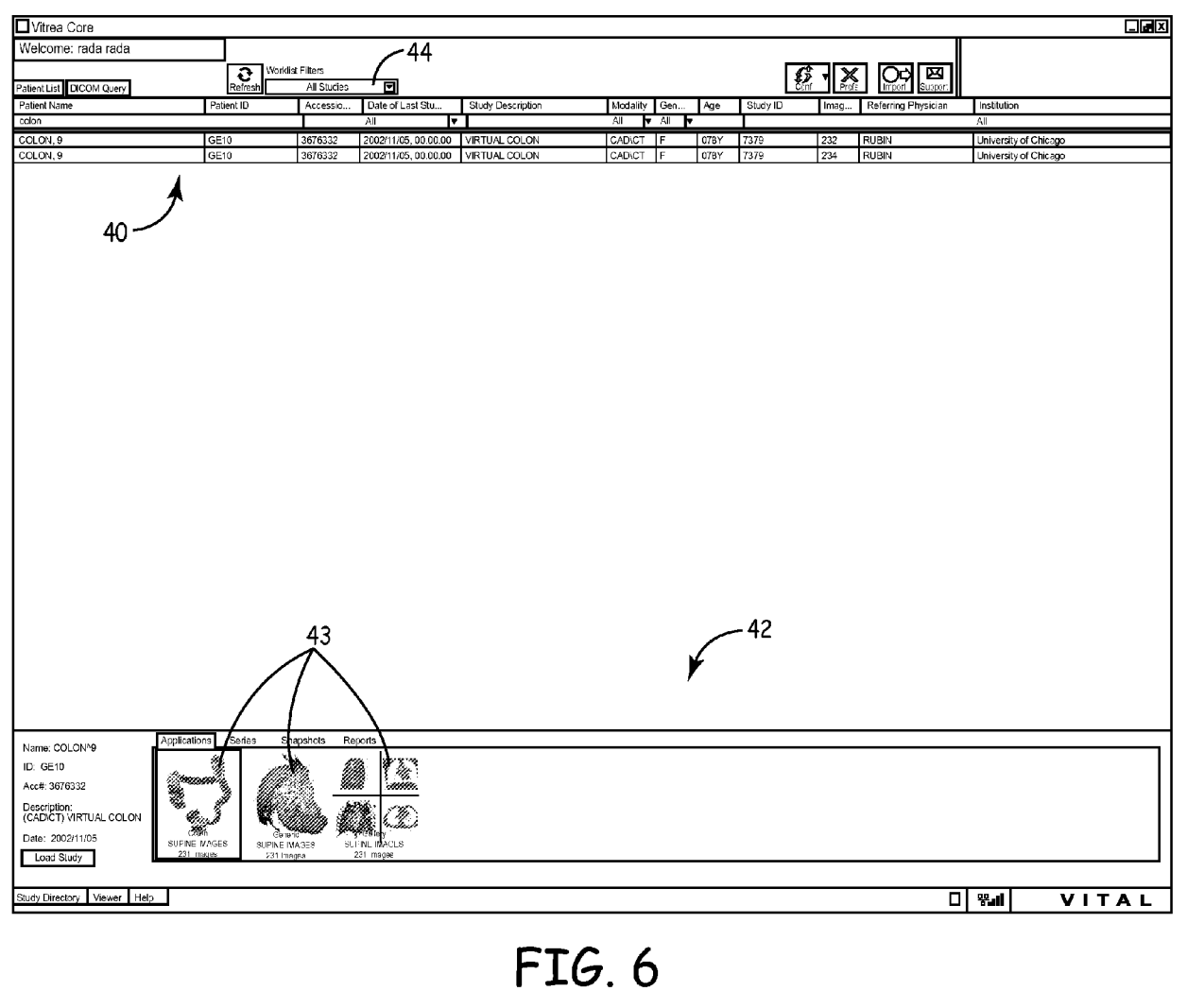

FIG. 6 is a screen shot of an example user interface including a colon study worklist 40 having a colon study selected and a data manager 42 including icons 43 for clinical applications associated with the selected colon study. Interaction with and options available through the user interface shown in FIG. 6 are substantially the same as the interaction and options described above with respect to the user interface in FIG. 2. For example, the filter menu 44 operates similarly to filter menu 14 described above.

When a user selects a study from the worklist 40, the controller 3 sends a signal to the imaging processor 5 to provide clinical applications and corresponding data sets for the selected study. The rule engine 8 retrieves the study image data from the database 6, which is provided to the imaging processor 5. The database 6 may also provide any preprocessed results (e.g., data sets identified from the study image data prior to storage in the database 6) that are associated with the study image data. The rule engine 8 then executes a set of rules that are programmed in the imaging processor 5 to the study image data and any preprocessed results to identify one or more clinical applications that may be run to analyze the data. The rule set that is retrieved and executed by the rule engine 8 may be selected based on the type of study selected by the user. Alternatively, the rule engine 8 may analyze the data retrieved from the image database 6 to identify the proper rule set.

Figure 7:
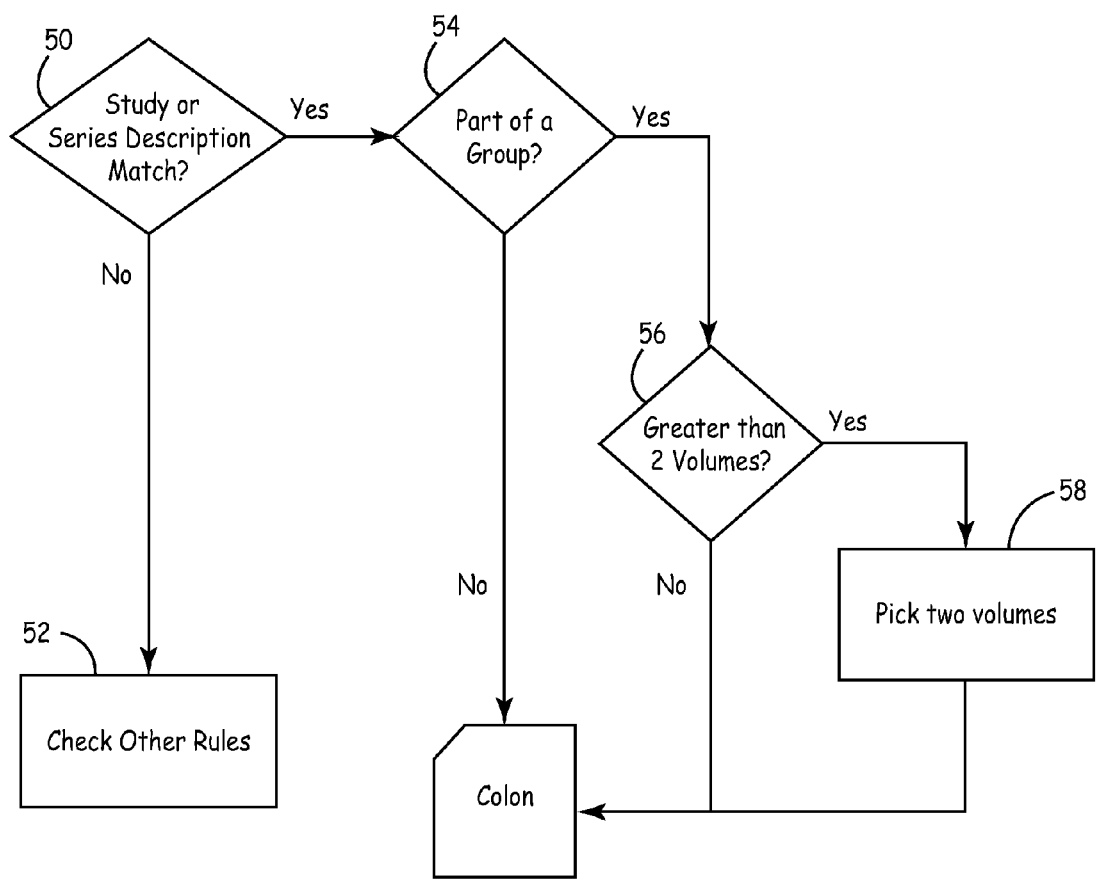
FIG. 7 is a flow diagram of a rules structure for selecting clinical applications and data sets from images associated a selected colon study.

FIG. 7 is a flow diagram of an exemplary rules structure for selecting data sets to associate with colon study applications from images associated with a selected colon study. In step 50, the rule engine 8 determines whether the description of the study or series matches the rules description. For example, in this embodiment, the rule engine 8 may search the "Study Description" field or other fields related to series associated with the selected study for words related to a colon study (e.g., colon, prone, supine, etc.) to determine whether the rule set based on the rules structure shown in FIG. 7 is appropriate. If words related to a colon study are not found in the searched field(s), then, in step 52, the rule engine 8 checks other rule sets for a match with the selected study.

If a colon study word is found in the searched field(s) of the selected study, then the rule engine 8 begins the process of identifying suitable clinical applications and associated data sets for the selected study. In step 54, the rule engine 8 determines whether the study includes a group of data sets. If the study does not include a group of data sets (i.e., the study includes just a single data set), the rule engine 8 associates the data set with the colon study clinical application and sends a signal to the controller 3 to display an icon for the colon clinical application on the data manager 42 and provides the data set to the controller 3.

If, in step 54, the rule engine 8 determines that the study includes multiple data sets, then, in step 56, the rule engine 8 determines whether the study includes more than a threshold number of data sets. In the embodiment shown in FIG. 7, the rule engine 8 determines whether the study includes more than two data sets. If the study includes two or fewer data sets, the rule engine 8 associates both data sets with the colon study clinical application and sends a signal to the controller 3 to display an icon for the colon clinical application on the data manager 42 and provides the two data sets to the controller 3.

If, in step 56, the rule engine 8 determines that the study includes more than two data sets, in step 58, the rule engine 8 selects two data sets from the set of data sets from the study. The selection may be based on an analysis of the image data. Alternatively, the rule engine 8 may select the first two data sets associated in the study. In any case, the rule engine 8 associates the selected data sets with the colon study clinical application and sends a signal to the controller 3 to display an icon for the colon clinical application on the data manager 42 and provides the two data sets to the controller 3.

The rules for selecting applications and image data for a colon study are expressed below in pseudocode. The pseudocode presented is not intended to be limiting, and rather is intended to illustrate one example approach to implementing the rules in the rule engine 8 described above.

```
RuleDef[ ] Study_Colon = new RuleDef[1];
Study_Colon[0] = new
RuleDef(SearchColumns.STUDY_DESCRIPTION,
    "Colon|Colo|Virtual", MatchType.kContainsOR);
addRule(ruleList, Study_Colon, "COLON_CT", "CT");
RuleDef[ ] Series_Colon = new RuleDef[1];
Series_Colon[0] = new
RuleDef(SearchColumns.SERIES_DESCRIPTION,
    "Colon|Colo|Virtual|Prone|Supine", MatchType.kContainsOR);
addRule(ruleList, Series_Colon, "COLON_CT", "CT");
RuleDef[ ] ACQ_Colon= new RuleDef[1];
ACQ_Colon[0] = new RuleDef(SearchColumns.PROTOCOL_NAME,
"Colon",
    MatchType.kContains);
addRule(ruleList, ACQ_Colon, "COLON_CT", "CT");
```

When the data set(s) associated with the colon clinical application have been identified, icons representing the identified clinical applications are displayed in the data manager 42. In the embodiment shown in FIG. 6, the rule engine 8 identified the generic and colon clinical applications as being suitable for the selected study. Icons representing each of these clinical applications are displayed in the data manager 42. Also provided with the icons 43 is an icon called "Gallery" that allows the user to review all data sets associated with the study, as generated by the imaging processor 5 during preprocessing of the image data.

The icons 43 are provided on a tab on the data manager 42 entitled "Applications." The data manager 42 may also include other tabs to provide access to the data associated with the selected study in other formats. For example, if the image data is stored in the image database 6 pursuant to the DICOM standard hierarchy, the data manager 42 may include a "Series" tab that allows the user to review the all series associated with the selected study. As discussed above, the data sets that are generated for use with the clinical applications may be generated from a single series of images, or may span across multiple series of images.

Figure 8:
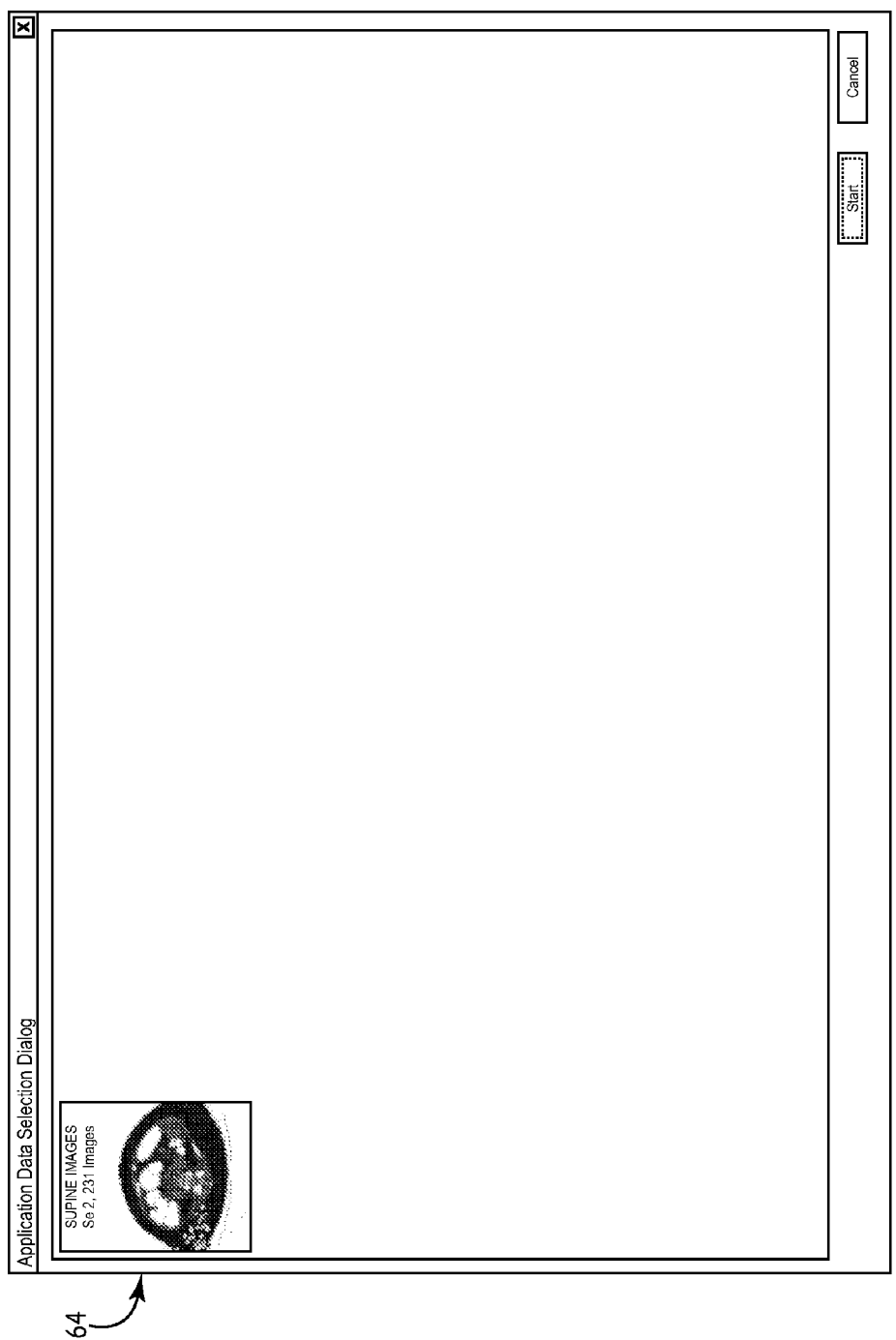
FIG. 8 is a screen shot of data sets related to a selected application in the data manager shown in FIG. 6.

The user may wish to review the data sets associated with each clinical application to make an independent assessment of the data set selection performed by the rule engine 8. FIG. 8 is a screen shot of the data set related to the colon clinical application in the data manager 42 shown in FIG. 6. The screen shot shown in FIG. 8 may accessed, for example, by right-clicking the colon clinical application to bring up a menu and selecting an option on the menu to review the data sets associated with the application. This allows the user to see the data set(s) that were identified as being the best match for the selected clinical application. In the embodiment shown, only a single data set was associated with the study, and this data set appears as icon 64 in FIG. 8. In cases including multiple identified data sets, each data set is displayed as an icon 64, and the user may select each of the different icons 64 to view the images associated with each of the data sets. If the user thinks that one of the data sets among the icons 64 is best suited for the selected application, the user may select the data set represented by the icon 64 to be analyzed by the selected clinical application.

Figure 9:
FIG. 9 is a screen shot of an application selected from the data manager in FIG. 6 loaded with a data set identified as suitable for the selected application.

When the user is satisfied with the data set(s) associated with a clinical application, the user may execute the clinical application with the selected volumetric data sets. The user may select the icon, which causes the controller 3 to begin analysis of the associated data set(s) of the clinical application. For example, FIG. 9 is a screen shot after the colon clinical application is selected from the data manager 42 in FIG. 6. In this case, the initiation of the colon clinical application brings up a set of tools that allows the clinician manipulate the identified data sets on the screen shown in FIG. 9 to analyze and assess various aspects cardiac function. For example, the clinician may use the application to determine information on the density of lesions and distance from the rectum. The tools for the colon function application also allow the clinician to tag and monitor polyps and other irregularities of the colon.

PET/CT Study Example

Figure 10:
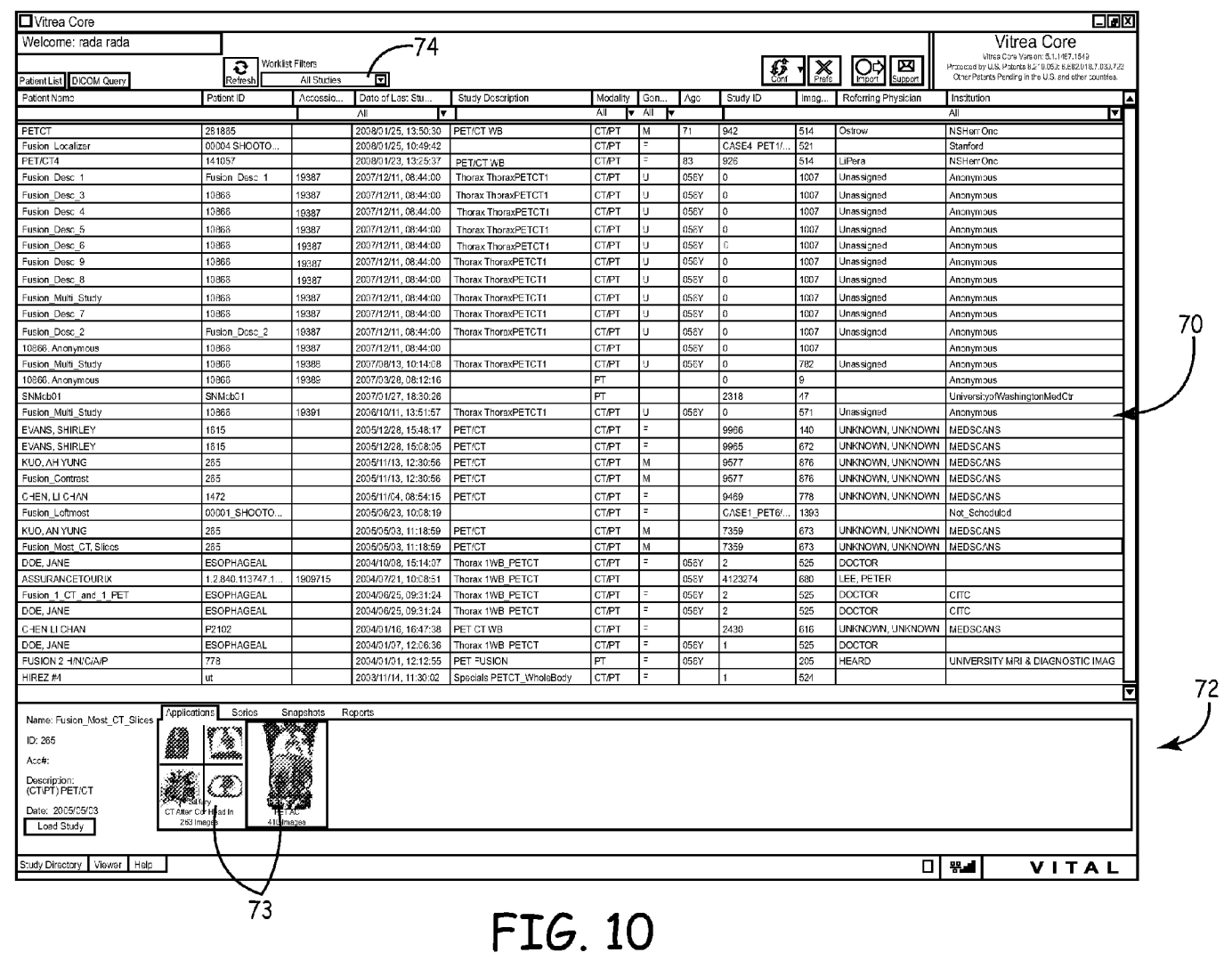

FIG. 10 is a screen shot of an example user interface including a PET/CT study worklist 70 having a PET/CT study selected and a data manager 72 including icons 73 for clinical applications associated with the selected PET/CT study. Interaction with and options available through the user interface shown in FIG. 10 are substantially the same as the interaction and options described above with respect to the user interface in FIG. 2. For example, the filter menu 74 operates similarly to filter menu 14 described above.

When a user selects a study from the worklist 70, the controller 3 sends a signal to the imaging processor 5 to provide clinical applications and corresponding data sets for the selected study. The rule engine 8 retrieves the study image data from the database 6, which is provided to the imaging processor 5. The database 6 may also provide any preprocessed results (e.g., data sets identified from the study image data prior to storage in the database 6) that are associated with the study image data. The rule engine 8 then executes a set of rules that are programmed in the imaging processor 5 to the study image data and any preprocessed results to identify one or more clinical applications that may be run to analyze the data. The rule set that is retrieved and executed by the rule engine 8 may be selected based on the type of study selected by the user. Alternatively, the rule engine 8 may analyze the data retrieved from the image database 6 to identify the proper rule set.

Figure 11:
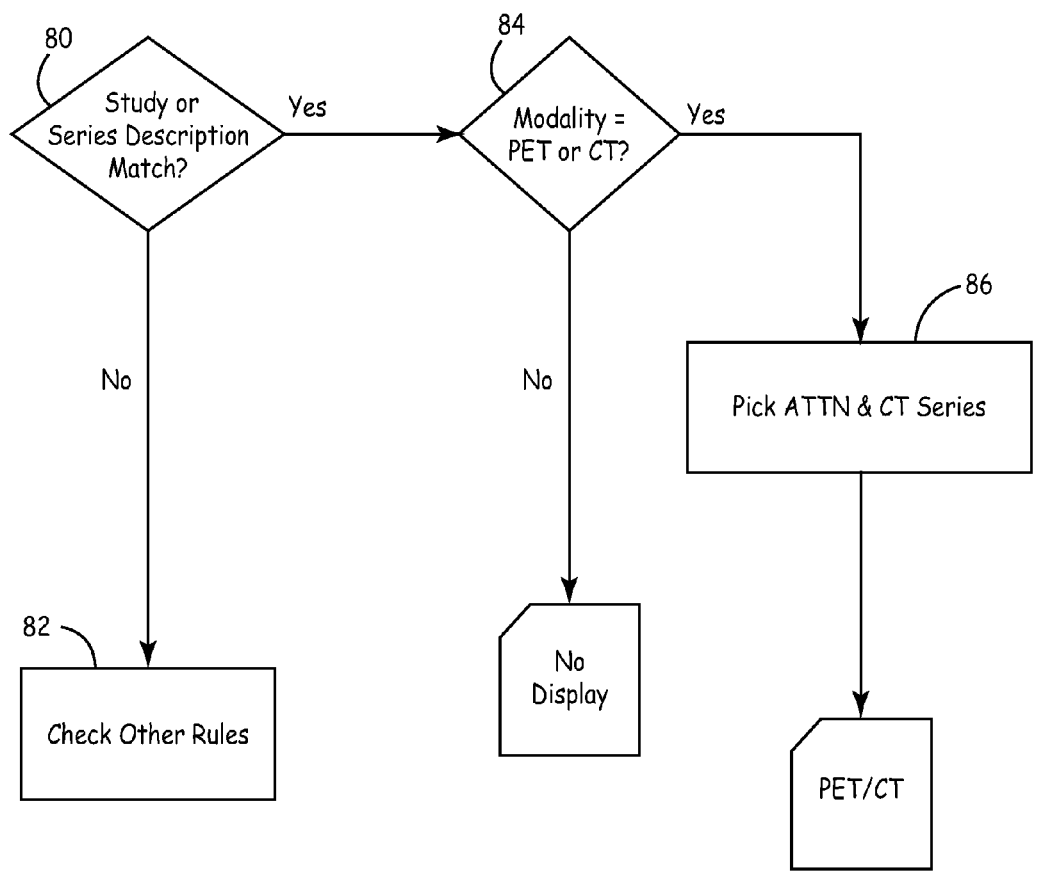
FIG. 11 is a flow diagram of a rules structure for selecting clinical applications and data sets from images associated with a selected PET/CT study.

FIG. 11 is a flow diagram of an exemplary rules structure for selecting data sets to associate with PET/CT study applications from images associated with a selected PET/CT study. In step 80, the rule engine 8 determines whether the description of the study or series matches the rules description. For example, in this embodiment, the rule engine 8 may search the "Study Description" field or other fields related to series associated with the selected study for words related to a colon study (e.g., PET/CT, tomography, etc.) to determine whether the rule set based on the rules structure shown in FIG. 11 is appropriate. If words related to a cardiac study are not found in the searched field(s), then, in step 82, the rule engine 8 checks other rule sets for a match with the selected study.

If a PET/CT study word is found in the searched field(s) of the selected study, then the rule engine 8 begins the process of identifying suitable clinical applications and associated data sets for the selected study. In step 84, the rule engine 8 determines whether the modality field for the study identifies the image data as being acquired in either a PET or CT scan. If modality field for the study indicates that the study does not include PET or CT images, the rule engine 8 determines that no clinical applications are suitable for the analyzing the data sets in the selected study.

If, on the other hand, the rule engine 8 determines that the study does include PET or CT image data in step 84, then, in step 86, the rule engine 8 selects two data sets from the set of data sets from the study, one of which is an attenuated corrected PET data set and the other of which is a CT data set. The identified data sets are associated with the PET/CT study clinical application by the rule engine 8. The rule engine 8 then sends a signal to the controller 3 to display an icon for the PET/CT clinical application on the data manager 72 and provides the data set to the controller 3.

The rules for selecting applications and image data for a PET/CT study are expressed below in pseudocode. The pseudocode presented is not intended to be limiting, and rather is intended to illustrate one example approach to implementing the rules in the rule engine 8 described above.

```
RuleDef[ ] Study_CT= new RuleDef[1];
Study_CT [0] = new RuleDef(SearchColumns.STUDY_DESCRIPTION,
"PETCT|PET/CT",
    MatchType.kContainsOR);
addRule(ruleList, Study_CT, "PET_CT", "CT");
RuleDef[ ] PET_AC= new RuleDef[1];
PET_AC [0] = new RuleDef(SearchColumns.CORRECTED_IMAGE,
"",
    MatchType.kContains);
addRule(ruleList, PET_AC, "PET_CT_AC", "PET|PT");
RuleDef[ ] Study_CT_NAC= new RuleDef[1];
Study_CT_NAC[0] = new
```

```
RuleDef(SearchColumns.STUDY_DESCRIPTION,
    "PETCT|PET/CT", MatchType.kContainsOR);
addRule(ruleList, Study_CT_NAC, "PET_CT_NAC", "CT");
RuleDef[ ] PET_NAC= new RuleDef[1];
PET_NAC[0] = new RuleDef(SearchColumns.CORRECTED_IMAGE,
"",
    MatchType.kContains);
addRule(ruleList, PET_NAC, "PET_CT_NAC", "PET|PT");
```

When the data set(s) associated with the PET/CT clinical application have been identified, a PET/CT icon representing the PET/CT clinical application is displayed in the data manager 72. Also provided with the icons 73 is an icon called "Gallery" that allows the user to review all data sets associated with the study, as generated by the imaging processor 5 during preprocessing of the image data.

The icons 73 are provided on a tab on the data manager 72 entitled "Applications." The data manager 72 may also include other tabs to provide access to the data associated with the selected study in other formats. For example, if the image data is stored in the image database 6 pursuant to the DICOM standard hierarchy, the data manager 72 may include a "Series" tab that allows the user to review the all series associated with the selected study. As discussed above, the data sets that are generated for use with the clinical applications may be generated from a single series of images, or may span across multiple series of images.

Figure 12:
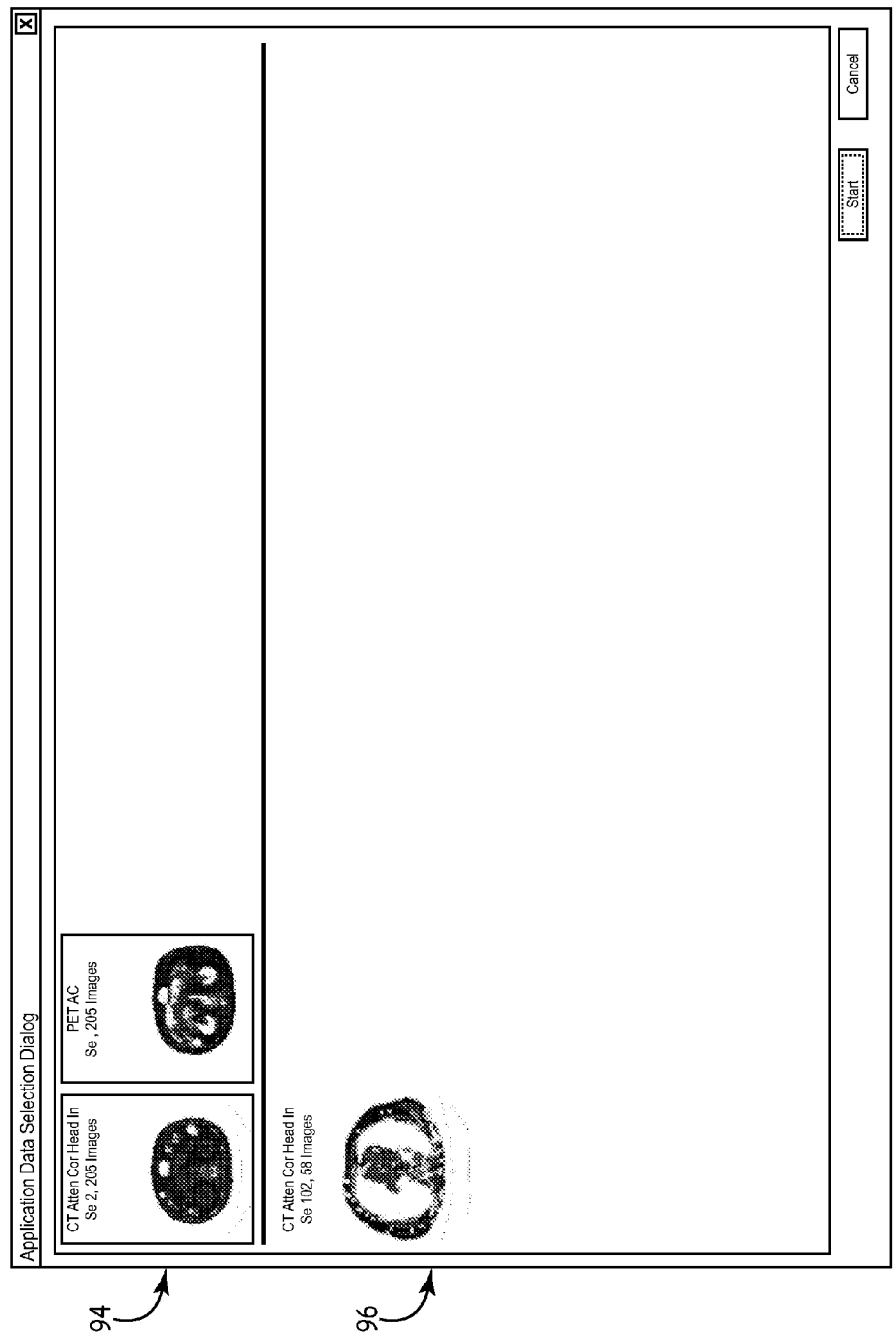
FIG. 12 is a screen shot of data sets related to a selected application in the data manager shown in FIG. 10.

The user may wish to review the data sets associated with each clinical application to make an independent assessment of the data set selection performed by the rule engine 8. FIG. 12 is a screen shot of data sets related to a selected application in the data manager 72 shown in FIG. 10. The screen shot shown in FIG. 12 may accessed, for example, by right-clicking the PET/CT clinical application to bring up a menu and selecting an option on the menu to review the data sets associated with the application. This allows the user to see the data set(s) that were identified as being the best match for the selected clinical application. This allows the user to see the data set(s) that were identified as being the best match for the selected clinical application. In FIG. 12, the two data sets that were identified by the rule engine 8 as being most suited for the selected clinical application are represented as icons 94, while other data sets that were not identified by the rule engine 8 as being suitable for the selected clinical application are shown on the bottom of the screen as icons 96. In some embodiments, a box surrounds the icons 94 to illustrate that the data sets associated with icons 94 are currently associated with the selected clinical application. The user may select each of the different icons 94, 96 to view the images associated with each of the data sets. If the user thinks that one of the data sets among the icons 96 is better suited for the selected clinical application, the user can override the rule engine 8 and identify a different data set to be displayed on the upper portion of the screen. The user may replace the data sets represented by icons 94 with one or more data sets represented by icons 96, or the user may add data sets represented by icons 96 to the data sets to be analyzed by the selected clinical application.

Figure 13:
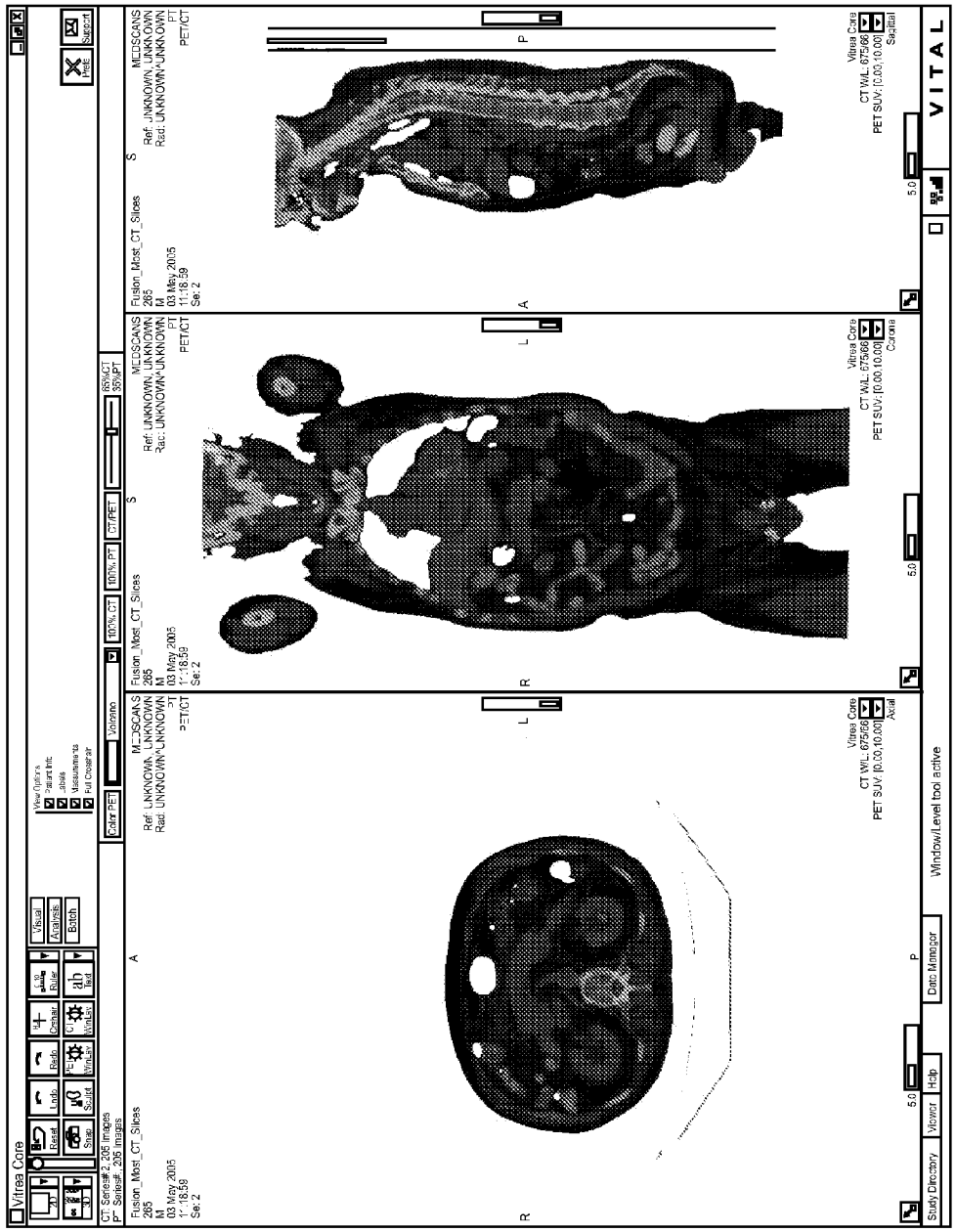
FIG. 13 is a screen shot of an application selected from the data manager in FIG. 10 loaded with a data set identified as suitable for the selected application.

When the user is satisfied with the data set(s) associated with a clinical application, the user may execute the clinical application with the selected volumetric data sets. The user may select the icon, which causes the controller 3 to begin analysis of the associated data set(s) of the clinical application. For example, FIG. 13 is a screen shot after the PET/CT clinical application is selected from the data manager 72 in FIG. 10. In this case, the initiation of the PET/CT clinical application brings up a set of tools that allows the user manipulate the identified data sets on the screen shown in FIG. 9 to analyze and assess the scanned anatomy. The user may also use tools provided by application to, for example, measure portions of the anatomy.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. A method for generating a user interface for selecting clinical applications in a medical imaging system, wherein the user interface is provided on a display and is responsive to user inputs in the medical imaging system, the method comprising:
    receiving a request to view a study including a plurality of images;
    acquiring the study to be viewed from a medical imaging system database;
    analyzing the acquired study with a rule engine that executes a plurality of applications rules on image data from the acquired study, wherein the rule engine identifies one or more clinical applications that are appropriate for the study, and wherein the rule engine further identifies at least one data set from the plurality of images suitable for each of the identified one or more clinical applications; and
    displaying one or more icons each associated with one of the identified one or more clinical applications, wherein each of the one or more icons is selectable on the user interface to initialize the associated clinical application.

2. The method of claim 1, and further comprising:
    displaying a gallery icon that provides access to all data sets associated with the study.

3. The method of claim 1, wherein the one or more icons are displayed on an applications tab on the user interface, wherein the user interface further comprises a series tab selectable to review all series in the study, and wherein each series is generated from the plurality of images.

4. The method of claim 1, wherein the at least one data set identified as being suitable for the clinical application is viewable via the icon associated with the clinical application.

5. The method of claim 4, wherein other data sets not identified as being suitable for the clinical application are viewable via the icon associated with the clinical application.

6. The method of claim 5, and further comprising:
    displaying the other data sets not identified as being suitable for the clinical application, wherein each of the other data sets is selectable to override the at least one data set identified as being suitable for the clinical application.

7. A user interface executing on a processor in a medical imaging system, wherein the user interface is provided on a display and is responsive to user inputs in the medical imaging system, the user interface comprising:
    a processor;
    a study worklist including a selectable list of one or more studies, each study including a plurality of images, wherein selection of a study in the study worklist causes the medical imaging system to acquire the study from a medical imaging system database; and
    a data manager including one or more icons each associated with a clinical application identified by the medical imaging system as being appropriate for the selected study, wherein each clinical application is associated with at least one data set in the study generated from the plurality of images and identified by the medical imaging system from the one or more series as being suitable for the identified clinical applications.

8. The user interface of claim 7, wherein the data manager includes a gallery icon that provides access to all data sets associated with the study.

9. The user interface of claim 7, wherein the one or more icons are displayed on an applications tab on the user interface, wherein the user interface further comprises a series tab selectable to review all series in the study, and wherein each series is generated from the plurality of images.

10. The user interface of claim 7, and further comprising:
a customization menu accessible via each of the one or more icons that, when selected, displays a customization screen including a data set icon associated with each of the identified at least one data set.

11. The user interface of claim 10, wherein the customization screen further includes additional data set icons associated with other data sets not identified by the medical imaging system as being suitable for the clinical application.

12. The user interface of claim 11, wherein each of the additional data set icons is selectable to override the at least one data set identified as being suitable for the clinical application.

13. The user interface of claim 7, wherein the one or more series comprises a plurality of series, and wherein the at least one data set spans across more than one of the plurality of series.

14. A medical imaging system comprising:
a medical imaging system database that stores one or more studies each including a plurality of images;
a processor that receives a request to view a study from an associated input device and accesses the medical imaging system database to acquire the requested study, the processor including a rule engine that executes a plurality of applications rules on image data from the acquired study, wherein the rule engine identifies one or more clinical applications that are appropriate for the study, and wherein the rule engine further identifies at least one data set from the plurality of images suited for each of the identified one or more clinical applications; and
a display connected to the processor that displays a user interface including one or more icons each associated with one of the identified one or more clinical applications, wherein each of the one or more icons is selectable on the user interface with the input device to initialize the associated clinical application.

15. The medical imaging system of claim 14, wherein the user interface further includes a gallery icon that provides access to all data sets associated with the selected study.

16. The medical imaging system of claim 14, wherein the one or more icons are displayed on an applications tab on the user interface, wherein the user interface further comprises a series tab selectable to review all series in the study, and wherein each series is generated from the plurality of images.

17. The medical imaging system of claim 14, wherein the user interface further includes a customization menu accessible via each of the one or more icons that, when selected, displays a customization screen including a data set icon associated with each of the identified data sets.

18. The medical imaging system of claim 17, wherein the customization screen further includes additional data set icons associated with other data sets not identified by the medical imaging system as being suitable for the clinical application.

19. The medical imaging system of claim 18, wherein each of the additional data set icons is selectable to override the at least one data set identified as being suitable for the clinical application.

20. The medical imaging system of claim 14, wherein the one or more series comprises a plurality of series, and wherein the at least one data set spans across more than one of the plurality of series.

* * * * *